United States Patent
Barnes

(10) Patent No.: US 7,384,737 B2
(45) Date of Patent: Jun. 10, 2008

(54) SYNTHESIS OF SPATIALLY ADDRESSED MOLECULAR ARRAYS

(75) Inventor: Colin Barnes, Nr. Saffron Walden (GB)

(73) Assignee: Solexa Limited, Nr. Saffron Walden, Essex (GB)

( * ) Notice: Subject to any disclaimer, the term of this patent is extended or adjusted under 35 U.S.C. 154(b) by 272 days.

(21) Appl. No.: 10/210,211

(22) Filed: Aug. 1, 2002

(65) Prior Publication Data

US 2003/0064398 A1 Apr. 3, 2003

Related U.S. Application Data

(63) Continuation of application No. PCT/GB01/00421, filed on Feb. 1, 2001.

(30) Foreign Application Priority Data

Feb. 2, 2000 (GB) ................................ 0002389.5

(51) Int. Cl.
*C12Q 1/68* (2006.01)
*C12M 1/36* (2006.01)
*C07H 21/04* (2006.01)

(52) U.S. Cl. ...................... 435/6; 435/91.1; 435/283.1; 536/23.1; 536/25.3

(58) Field of Classification Search ................ 435/6, 435/7.1, 174, 283.1, 91.1, 287.2; 536/23.1, 536/25.3
See application file for complete search history.

(56) References Cited

U.S. PATENT DOCUMENTS

| 5,302,509 | A | | 4/1994 | Cheeseman | 435/6 |
| 5,843,655 | A | * | 12/1998 | McGall | 506/16 |
| 6,136,543 | A | * | 10/2000 | Anazawa et al. | 435/6 |
| 6,221,592 | B1 | * | 4/2001 | Schwartz et al. | 435/6 |
| 6,245,518 | B1 | * | 6/2001 | Baier | 435/6 |
| 6,818,395 | B1 | * | 11/2004 | Quake et al. | 435/6 |

FOREIGN PATENT DOCUMENTS

| EP | 0 955 085 A2 | 11/1999 |
| WO | WO 90/13666 | 11/1990 |
| WO | WO 90/15070 | 12/1990 |
| WO | WO 92/10092 | 6/1992 |
| WO | WO 92/10587 | 6/1992 |
| WO | WO 93/06121 | 4/1993 |
| WO | WO 95/12608 | 5/1995 |
| WO | WO 96/12014 | 4/1996 |
| WO | WO 96/27025 | 9/1996 |
| WO | WO 98/20019 | 5/1998 |
| WO | WO 99/05315 | 2/1999 |
| WO | WO 00/06770 | 2/2000 |

OTHER PUBLICATIONS

Huber et al "Monitoring solid phase synthesis by infrared spectroscopic techniques" Analytica Chemica Acta, 1999 393: 213-221.*
Weiss "Fluoresscence Spectroscopy of Single Biomolecules" Science, Mar. 12, 1999 283: 1676-1683.*
Joos et al "Covalent Attachment of Hybridizable Oligonucleotides to Glass Supports" Analytical Biochemistry, 1997, 247: 96-101.*
Seeger, S. (1998). "Einzelmolekuelfluoreszenz. Molekular Hochleistungsdiagnostik Und Wirkstoffscreening," *Bioforum, De, Git Verlag, Darmstadt,* 21(4):179-180, 182-185 (English Translation enclosed).
Rigler, R. (1995). "Fluorescence correlations, single molecula detection and large number screening—Applications in biotechnology," *Journal of Biotechnology, NL, Elsevier Science Publishers, Amsterdam,* 41(2):177-186.
International Search Report of International Application No. PCT/GB 01/00421.
International Search Report of International Application No. PCT/GB 01/00421, 2001.

* cited by examiner

*Primary Examiner*—B J Forman
(74) *Attorney, Agent, or Firm*—Klauber & Jackson LLC

(57) ABSTRACT

Methods are disclosed for forming spatially addressable arrays of polynucleotides of known squence, by using blocking groups that prevent the incorporation of multiple nucleotides during each incorporation step.

10 Claims, No Drawings

SYNTHESIS OF SPATIALLY ADDRESSED MOLECULAR ARRAYS

FIELD OF THE INVENTION

This invention relates to fabricated arrays of polymers. In particular, this invention relates to the production of spatially addressed polymer arrays.

BACKGROUND OF THE INVENTION

Advances in the study of molecules have been led, in part, by improvement in technologies used to characterise the molecules or their biological reactions. In particular, the study of nucleic acid, DNA and RNA, has benefitted from developing technologies used for sequence analysis and the study of hybridisation events.

An example of the technologies that have improved the study of nucleic acids, is the development of fabricated arrays of immobilised nucleic acids. These arrays typically consist of a high-density matrix of polynucleotides immobilised onto a solid support material. Fodor et al., Trends in Biotechnology (1994) 12:19-26, describes ways of assembling the nucleic acid arrays using a chemically sensitised glass surface protected by a mask, but exposed at defined areas to allow attachment of suitably modified nucleotides.

An alternative approach is described by Schena et al., Science (1995) 270:467-470, where samples of DNA are positioned at predetermined sites on a glass microscope slide by robotic micropipetting techniques. The DNA is attached to the glass surface through its entire length by non-covalent electrostatic interactions.

The arrays are usually provided to study hybridisation events, determine the sequence of DNA (Mirzabekov, Trends in Biotechnology (1994) 12:27-32) or to detect mutations in a particular DNA sample. Many of these hybridisation events are detected using fluorescent labels attached to nucleotides with fluorescence detected using sensitive fluorescent detector, e.g. charge coupled detector (CCD). However, the major disadvantages of these methods are that it is not possible to sequence long stretches of DNA and repeat sequences can lead to ambiguity in the results. These problems are recognised in Automation Technologies for Genome Characterisation, Wiley—Interscience, 1997, Ed. T. J. Beugelsdijk, Chapter 10: 205-225.

In addition, the use of multi-molecule high-density arrays in a multi-step analysis procedure can lead to problems with phasing. Phasing problems result from a loss in the synchronisation of a reaction step occurring on different molecules of the array. If a proportion of the arrayed molecules fails to undergo a step in the procedure, subsequent results obtained for these molecules will no longer be in-step with results obtained for the other arrayed molecules. The proportion of molecules out of phase will increase through successive steps and consequently the results detected will become ambiguous. This problem is recognised in the sequencing procedure described in U.S. Pat. No. 5,302,509.

SUMMARY OF THE INVENTION

According to the present invention, a method for forming a spatially addressable array of polymers immobilised on a solid support comprises the steps of:

(i) contacting an array of single molecules with one or more detectably labelled monomers, under conditions that permit incorporation of a monomer onto a molecule of the array, wherein the labelled monomer comprises a removable blocking group that prevents further monomer incorporation occurring;

(ii) removing non-incorporated monomers and detecting the label on the incorporated monomer;

(iii) removing the blocking group and any separate label; and (iv) optionally repeating steps (i)-(iii) to form a single polymer of defined sequence;

wherein the array has a surface density which allows each polymer to be individually resolved by optical microscopy.

According to the present invention, high-density single polymer arrays are synthesised in a manner that permits the sequence of each polymer to be determined. As the sequence for each polymer is known, the result of the synthesis is a spatially addressed array. Further, the random addition of monomers to the growing polymer strands in the synthesis procedure allows a vast diversity of different polymers to be formed.

The formation of spatially addressed high-density arrays has many important benefits for the study of the single polymer molecules and their interactions with other biological molecules. The arrays are particularly suitable for DNA analysis procedures using hybridisation-based approaches. Knowing the sequence of polynucleotides (polymers) on the array enables the user to quickly determine the sequence of a complementary polynucleotide hybridised thereto.

DESCRIPTION OF THE INVENTION

The present invention relates to the formation of single molecule polymer arrays using a step-wise synthesis procedure, whereby the identity of each monomer is determined at each incorporation step.

The term "single molecule" and "single polymer" is used herein to distinguish from high-density, multi-molecule arrays in the prior art, which may comprise distinct clusters of many molecules of the same type.

The term "individually resolved" is used herein to indicate that, when visualised, it is possible to distinguish one polymer on the array from its neighbouring polymers. Visualisation may be effected by the use of reporter labels, e.g. fluorophores, the signal of which is individually resolved. The requirement for individual resolution ensures that individual monomer incorporation can be detected at each synthesis step.

In general, the method may be carried out using conventional synthesis techniques which utilise the step-wise incorporation of monomers onto a growing polymer strand.

The synthesised polymers may be of any biomolecule or organic molecule, including peptides and polypeptides. The polymers are preferably polynucleotides, e.g. DNA or RNA, and the monomers for incorporation may be the bases adenine (A), thymine (T), guanine (G) and cytidine (C). Uracil (U) may also be used.

The monomers should be detectably-labeled and include a blocking group to prevent incorporation of further monomers until after the detection step has been carried out. In one preferred embodiment, the label is, or is part of, the blocking group, and can be removed under defined conditions. Different monomer types will usually be labeled with a distinct label. For example, in the context of DNA synthesis, each monomer base will have a specific label which characterises the base. This enables the stepwise incorporation of monomers to be monitored during the synthesis procedure.

Preparation of monomers with suitable labels and blocking groups will be apparent to the skilled person. For DNA, conventional phosphoramidite chemistries may be used. The label (fluorophore) may be located on a protecting group or may be located at a separate position. A skilled person will appreciate that cleavable linker groups can be readily prepared, as in U.S. Pat. No. 5,302,509.

Suitable labels will also be apparent to the skilled person. In a preferred embodiment, the label is a fluorophore. Alternative labels may be used. A number of strategies for labelling molecules of DNA have been reported, such as microspheres (Anal. Chem. (2000) 72, 15: 3678-3681), gold nanoparticles (J. Am. Chem. Soc, (2000) 122, 15: 3795-3796), silver colloid particles (PNAS, (2000) 97, 3: 996-1001) and quantum dots. Any labelling technique that allows unambiguous identification of the incorporated moiety can be utilised in this scheme.

The first step in the synthesis procedure will be to form an array of single molecules, onto which the monomers are to be incorporated. Immobilisation of the single molecules to the surface of a solid support may be carried out by any known technique. Generally the array is produced by dispensing small volumes of a sample onto a suitably prepared solid surface, or by applying a dilute solution to the solid surface to generate a random array. Immobilisation may occur by covalent or non-covalent interactions.

The single molecules may themselves be monomers, prepared so that immobilisation with the solid support can occur. If the molecule is a monomer base, immobilisation will preferably occur at the 3'-position to permit incorporation at the 5'-position. Various linker molecules, e.g. polyethylene glycol, may also be present. Further details of the preparation of these single molecule arrays is disclosed in WO-A-00/06770.

If the polymer is a polynucleotide, synthesis may be carried out by the use of conventional solid-phase DNA synthesis techniques, e.g. using phosphoramidite chemistry as disclosed in "Nucleic Acids in Chemistry and Biology" by Blackburn & Gait, Oxford University Press, pages 118-137, Tetrahedron Letters (1990) 31 49: 7095-7098, and Tetrahedron Letters (2000) 56: 2713-2724. If a fluorescently-modified 5'-protecting group is used with the phosphoramidite, then the deprotection and removal of the fluorescent label can be carried out in a single step after each round of synthesis. Each round of synthesis may comprise one or more different monomers, e.g. the bases G, C, A and T. The array may be synthesised randomly by incorporating all the different monomers during each round of synthesis, or in a more controlled fashion, using only one distinct monomer in each round of synthesis.

The density of the arrays is not critical. However, the present invention can make use of a high-density of single polymer molecules, and these are preferable. For example, arrays with a density of $10^6$-$10^9$ polymers per $cm^2$ may be used. Preferably, the density is at least $10^7/cm^2$ and typically up to $10^8/cm^2$. These high-density arrays are in contrast to other arrays which may be described in the art as "high-density" but which are not necessarily as high and/or which do not allow single molecule resolution.

The extent of separation between the individual polymers on the array will be determined, in part, by the particular technique used to resolve the individual polymer molecule. Apparatus used to image molecular arrays are known to those skilled in the art. For example, a confocal scanning microscope may be used to scan the surface of the array with a laser to image directly a fluorophore incorporated on the individual polymer by fluorescence. Alternatively, a sensitive 2-D detector, such as a charge-coupled detector, can be used to provide a 2-D image representing the individual polymers on the array.

Resolving single polymer molecules on the array with a 2-D detector can be done if, at 100× magnification, adjacent polymers are separated by a distance of approximately at least 250 nm, preferably at least 300 nm and more preferably at least 350 nm. It will be appreciated that these distances are dependent on magnification, and that other values can be determined accordingly, by one of ordinary skill in the art.

Other techniques such as scanning near-field optical microscopy (SNOM) are available which are capable of greater optical resolution, thereby permitting more dense arrays to be used. For example, using SNOM, adjacent polymers may be separated by a distance of less than 100 nm, e.g. 10 nm. For a description of scanning near-field optical microscopy, see Moyer et al., Laser Focus World (1993) 29(10).

An additional technique that may be used is surface-specific total internal reflection fluorescence microscopy (TIRFM); see, for example, Vale et al., Nature, (1996) 380: 451-453). Using this technique, it is possible to achieve wide-field imaging (up to 100 μm×100 μm) with single polymer molecule sensitivity. This may allow arrays of greater than $10^7$ resolvable polymers per $cm^2$ to be used.

Additionally, the techniques of scanning tunnelling microscopy (Binnig et al., Helvetica Physica Acta (1982) 55:726-735) and atomic force microscopy (Hansma et al., Ann. Rev. Biophys. Biomol. Struct. (1994) 23:115-139) are suitable for imaging the arrays of the present invention. Other devices which do not rely on microscopy may also be used, provided that they are capable of imaging within discrete areas on a solid support.

Suitable solid supports are available commercially, and will be apparent to the skilled person. The supports may be manufactured from materials such as glass, ceramics, silica and silicon. The supports usually comprise a flat (planar) surface, or at least an array in which the polymers are in the same plane. Any suitable size may be used. For example, the supports might be of the order of 1-10 cm in each direction.

It is important to prepare the solid support under conditions which minimise or avoid the presence of contaminants. The solid support must be cleaned thoroughly, preferably with a suitable detergent, e.g. Decon-90, to remove dust and other contaminants.

Because the array consists of optically resolvable polymers, the synthesis of each target polymer will generate a series of distinct signals as the fluorescent events are detected. Details of the full sequence may then be determined.

The sequence of the polymers is determined by the random incorporation of the monomers and not by the presence of any template molecule. Sequencing procedures are therefore not required, i.e. procedures requiring the use of the polymerase enzyme.

The arrays of the invention are particularly suitable for analysis procedures where the spatially addressable polymers can be used to reveal information on an interacting molecule. For example, if the polymers are polynucleotides, the arrays may be used in hybridisation-based procedures, to reveal the sequence of target DNA which hybridises on the array. Uses of spatially addressed arrays are disclosed in WO-A-00/06770.

The invention claimed is:

1. A method for forming a spatially addressed array of a plurality of single polymers, wherein the polymers are polynucleotides immobilized on a single solid support, and wherein the solid support is a planar surface comprising the steps of:

(i) contacting the array of single molecules with one or more detectably labeled monomers, under conditions that permit template independent incorporation of a monomer onto a molecule of the array, wherein the labelled monomer comprises a removable blocking group that prevents further monomer incorporation occurring;

(ii) removing non-incorporated monomers from the array of single molecules and detecting the label on the incorporated monomer;

(iii) removing the blocking group and any separate label; and (iv) repeating steps (i)-(iii) to form single polymers of defined sequence; wherein the array has a surface density which allows each polymer to be individually resolved by optical microscopy and each of the polymers is synthesized by template independent random incorporation of said labeled monomers, and wherein a spatially addressed array of single polymers is formed by determining the sequence of each single polymer on the array via detection of incorporated monomers.

2. A method according to claim 1, wherein the detectably labeled monomers are any of the bases A, C, T and G.

3. A method according to claim 2, wherein each of the bases A, C, T and G comprises a different label, and step (i) is carried out in the presence of all four bases.

4. A method according to claim 1, wherein the label is a fluorophore.

5. A method according to claim 4, wherein the label is detected using a 2-D fluorescent imaging device, a confocal fluorescence microscope or a CCD camera.

6. A method according to claim 5, wherein the label is removed by chemical or enzymatic cleavage.

7. A method according to claim 6, wherein the array has a density of from $10^5$ to $10^9$ polymers per cm$^2$.

8. A method according to claim 7, wherein the density is $10^7$ to $10^8$ polymers per cm$^2$.

9. A method according to claim 8, wherein the polymers are separated by a distance of at least 100 nm.

10. A method according to claim 9, wherein the polymers are separated by a distance of at least 250 nm.

* * * * *